(12) United States Patent
Ishibiki

(10) Patent No.: US 6,923,758 B2
(45) Date of Patent: Aug. 2, 2005

(54) ENDOSCOPE

(75) Inventor: Kota Ishibiki, Hachioji (JP)

(73) Assignee: Olympus Corporation, Tokyo (JP)

( * ) Notice: Subject to any disclaimer, the term of this patent is extended or adjusted under 35 U.S.C. 154(b) by 261 days.

(21) Appl. No.: 10/295,778

(22) Filed: Nov. 15, 2002

(65) Prior Publication Data

US 2003/0149339 A1 Aug. 7, 2003

(30) Foreign Application Priority Data

Nov. 22, 2001 (JP) ........................................ 2001-358029

(51) Int. Cl.$^7$ ................................................. A61B 1/00
(52) U.S. Cl. ........................ 600/133; 600/109; 600/177
(58) Field of Search ................................. 600/109, 133, 600/160, 161, 169, 176, 177

(56) References Cited

U.S. PATENT DOCUMENTS 6,767,322 B1 * 7/2004 Futatsugi et al. ........... 600/133

FOREIGN PATENT DOCUMENTS

| JP | 2000-135196 | 5/2000 |
|---|---|---|
| JP | 2000-342512 | 12/2000 |

* cited by examiner

*Primary Examiner*—Beverly M. Flanagan
(74) *Attorney, Agent, or Firm*—Straub & Pokotylo; John C. Pokotylo

(57) ABSTRACT

An illuminational optical system and an observational optical system mounted to lens frames are arranged at the tip part of an insertion portion. The observational optical system has resistance to high-temperature steam sterilization, and is sealed steam-tight in order to avoid entering of steam into the inside. On the other hand, the illuminational optical system is sealed liquid-tight with an adhesive, and even when steam enters into the inside, the entered steam can be discharged by the heat accompanying illumination light during an endoscope inspection. Consequently, cost reduction can be achieved and repairability, etc., can be ensured with almost no degradation in observation performance.

21 Claims, 8 Drawing Sheets

ENDOSCOPE

This application claims benefit of Japanese Patent Application No. 2001-358029 filed on Nov. 22, 2001, the contents of which are incorporated by this reference.

BACKGROUND OF THE INVENTION

Field of the Invention and Description of the Related Art

The present invention relates to an endoscope adaptable to high-temperature high-pressure steam sterilization primarily used for medical application. In particular, the present invention relates to an endoscope, inexpensive, in which observation performance is not degraded even when high-temperature high-pressure steam sterilization is performed, and repairability, moisture resistance, durability, and operability can be improved.

Conventionally, regarding endoscopes widely used for medical application, observation of organs in the body cavity, etc., can be performed and, if necessary, various therapies and treatments can be performed using a slender insertion portion of therapeutic instruments being inserted through the therapeutic instrument channel in the body cavity. Furthermore, in the industrial field, endoscopes for industrial use capable of performing observation and inspection of flaws, corrosions, etc., of the inside of boilers, turbines, engines, chemical plants, etc., have been widely used.

In particular, regarding the endoscope used in a medical field, the insertion portion is inserted in the body cavity, and thereby, organs, etc., are observed and various therapies and treatments are performed using therapeutic instruments inserted through the therapeutic instrument channel of the endoscope. Consequently, when an endoscope and therapeutic instrument used once are reused for other patients, it is necessary to perform cleaning and disinfection of the endoscope apparatus after an inspection and treatment has been completed for reasons of necessity to prevent cross infection between patients through the endoscope and therapeutic instrument.

As a disinfection and sterilization treatment of these endoscopes and accessories thereof, conventionally, a disinfection and sterilization treatment method using a gas, for example, ethylene oxide gas (EOG), and a disinfectant has been performed. There was a problem in that since aeration for removing gases adhered to the equipment after sterilization takes much time, the equipment is not able to use immediately after the sterilization. Furthermore, there is a problem in that the running cost is high. On the other hand, regarding the disinfectant, there are problems in that management of the disinfectant is complicated, and disposal of the disinfectant requires a significant cost.

In recent years, autoclave sterilization (high-temperature high-pressure steam sterilization) has become the mainstream of the disinfection and sterilization treatments of medical equipment, wherein no complicated operation attends, it is possible to use immediately after sterilization, and the running cost is low.

However, the high-temperature high-pressure steam has a property of passing through materials primarily containing macromolecular materials, for example, rubber, elastomer, and resin member, or through adhesives. In particular, flexible materials, for example, rubber and elastomer, are generally likely to pass steam. Among them, especially, silicone rubber-based materials have very high permeability to steam.

Consequently, regarding conventional endoscopes having a water-tight structure composed of O-rings made of silicone rubber, silicone based-adhesive, etc., the high-temperature high-pressure steam enters inside the endoscopes during autoclave sterilization.

Not limited to the aforementioned silicone rubber, even O-rings made of fluororubber, epoxy-based adhesives, and furthermore, other various macromolecular materials pass steam, although the level is low compared with that of the silicone rubber. That is, in order to prevent entering of steam inside the endoscope during autoclave sterilization, extremely high airtightness is required compared with conventional watertightness that prevents entering of chemical solutions even when immersed in the chemical solutions or airtightness at usual atmospheric pressure.

General materials which do not pass the high-temperature high-pressure steam under the conditions stipulated by current US standards, etc., are limited to the materials selected from metals, ceramic, glass, and crystalline materials. Junction devices for joining materials to each other are also limited to the junction methods, for example, soldering, in which primary component of the joint portion are metals, ceramic, glass, and crystalline materials.

In consideration of these requirements, conventionally, many suggestions have been made. Examples of related arts include, for example, endoscopes described in Japanese Unexamined Patent Application Publication No. 2000-342512 and Japanese Unexamined Patent Application Publication No. 2000-135196.

Regarding the endoscope in Japanese Unexamined Patent Application Publication No. 2000-342512, an objective lens frame provided with a tip lens and an objective lens as optical members and a cover glass frame provided with a cover glass are fitted to a pipe-shaped hollow cylindrical member, the objective lens frame and the cover glass frame are individually joined to the aforementioned cylindrical member and, therefore, an observational optical system unit is configured. Consequently, since the outer diameter at the tip side of the endoscope insertion portion is a reduced diameter, even when the autoclave sterilization is performed, entering of steam into the observational optical system unit can be prevented.

On the other hand, regarding the endoscope in Japanese Unexamined Patent Application Publication No. 2000-135196, the endoscope includes a fiber bundle formed by bundling a plurality of element fibers and a lens group which is arranged at the end portion of the aforementioned fiber bundle and which is composed of one or more than one lens, and in the configuration thereof, a filler for keeping airtightness is put into at least among the fibers of the tip portion of the aforementioned fiber bundle, and all of the joint portions between the end portion of the fiber bundle filled with this filler for keeping airtightness and an optical window arranged at the extreme tip of the aforementioned lens group are joined airtight. According to this, entering of steam into the optical path between the fiber end portion and the optical window during the autoclave sterilization is prevented with reliability and, therefore, the endoscope adaptable to the autoclave sterilization can be realized.

However, regarding the endoscope adaptable to the high-temperature high-pressure steam sterilization of the related art example, in the case of a common steam-tight structure, steam of the high-temperature high-pressure steam sterilization may enter into the optical path between the optical members and, thereby, observation performance is adversely affected. On the other hand, as shown in the aforementioned Japanese Unexamined Patent Application Publication No. 2000-135196, the endoscope having a structure in which all of the optical members are joined steam-tight with respect to steam of the high-temperature high-pressure steam sterilization can prevent entering of steam into the optical path between the optical members during the high-temperature high-pressure steam sterilization (autoclave sterilization) with reliability. On the other hand, since the number of steps of steam-tight junction is increased and the operation thereof becomes complicated, it is difficult to improve ease of assembling and, as a result, the assembling cost and the manufacturing cost are increased. Regarding the junction method, when a method of laser welding, soldering, brazing, or the like is performed, there is an inconvenience that disassembling of individual primary components became difficult and, therefore, repairability was adversely affected.

General materials, which do not pass the high-temperature high-pressure steam with respect to the steam of the high-temperature high-pressure steam sterilization, are limited to the materials selected from metals, ceramic, glass, and crystalline materials, and the materials primarily containing macromolecular materials, for example, rubber and resin, are likely to pass the steam.

Consequently, in the endoscope adaptable to the high-temperature high-pressure steam sterilization of the related art example, regarding the sealing part in the movable portion, it is difficult to seal thereof with the aforementioned materials which do not pass the high-temperature high-pressure steam. When high-hardness fluororubber, etc., which are relatively unlikely to pass the steam are used, there is an inconvenience that it is difficult to allow the movable portion to have excellent operability. It is feared that the steam entered inside the endoscope from the sealing portion, for example, O-rings, and in this case, it is also feared that moisture is accumulated and, therefore, the durability is adversely affected. Furthermore, since the fitted portion of a folding-preventing member on the insertion portion and a flexible tube portion is liquid-tight, it is feared that the steam entered into the inside through the sealing portion and the material itself during high-temperature high-pressure steam sterilization is not discharged. In this case, when repeatedly performed, this is accumulated and, therefore, it is feared that the metal components arranged in this space are corroded, the resin constituting the flexible tube is hydrolyzed and degraded so as to bring about cracks, etc., and, therefore, there is an inconvenience that especially the portion tightened by the folding-preventing member is likely to break.

OBJECT AND SUMMARY OF THE INVENTION

It is an object of the present invention to provide an endoscope, inexpensive, in which observation performance is not degraded even when high-temperature high-pressure steam sterilization is performed, and repairability can be improved.

An endoscope is configured to include a slender insertion portion, an illuminational optical system which is arranged at the tip portion of the aforementioned insertion portion and which emits transmitted illumination light onto a subject side, a first frame member in which the aforementioned illuminational optical system is fitted, an observational optical system for forming an optical image of the subject illuminated by the aforementioned illuminational optical system, a second frame member in which the aforementioned observational optical system is fitted, a liquid-tight joint portion which is arranged at the end portion facing the outside of the aforementioned first frame member and which is joined liquid-tight to a first lens member constituting the aforementioned illuminational optical system and the aforementioned first frame member, and a steam-tight joint portion which is arranged at the end portion facing the outside of the aforementioned second frame member and which is joined steam-tight to a second lens member constituting the aforementioned observational optical system and the aforementioned second frame member, and, thereby, entering of steam into the observational optical system can be prevented, and fogging of the observational optical system does not occur. The steam may enter into the observational optical system. However, even when fogging occurs, the fogging does not affect the illumination performance, drying can also be performed by the heat of illumination light supplied during inspection and, therefore, stabilization of the observation performance can be achieved. Furthermore, the illuminational optical system portion can be inexpensively configured, disassembly can be performed with ease, and repairability can be improved.

BRIEF DESCRIPTION OF THE DRAWINGS

FIG. 1 to FIG. 5B relate to a first embodiment of the present invention, and FIG. 1 is a configurational diagram showing the overall configuration of an endoscope apparatus provided with the first embodiment.

FIG. 2 is a longitudinal sectional view of an endoscope tip portion of the first embodiment.

FIG. 3 is a sectional view of the observational optical system unit shown in FIG. 2.

FIG. 4 is a sectional view showing an objective lens frame in which a tip lens of the observational optical system is fitted.

FIG. 5B is a sectional view showing the tip lens provided with a surface treatment layer under magnification.

FIG. 8 is a partially cutaway sectional view in the neighborhood of a connector.

FIG. 9 is a sectional view in the neighborhood of the connector during a waterproof test.

FIG. 10 is a sectional view in the neighborhood of the connector during pressurization by high-temperature high-pressure steam sterilization.

FIG. 11 is a sectional view in the neighborhood of the connector during depressurization by high-temperature high-pressure steam sterilization.

FIG. 12 is a longitudinal sectional view of an insertion portion folding-preventing member of the insertion portion of an endoscope according to the sixth embodiment.

FIG. 13 is an illustrative diagram showing the condition that an endoscope is stored in a storage case for sterilization.

FIG. 14 is an illustrative diagram for explaining the condition that the insertion portion folding-preventing member is regulated by a regulation portion arranged in the storage case for sterilization shown in FIG. 13.

DESCRIPTION OF THE EMBODIMENTS

The embodiments of the present invention will be described below with reference to the drawings.
(First Embodiment)

The first embodiment of the present invention will be described with reference to FIG. 1 to FIG. 5B.

Initially, the configuration thereof will be described.

Figure 1:
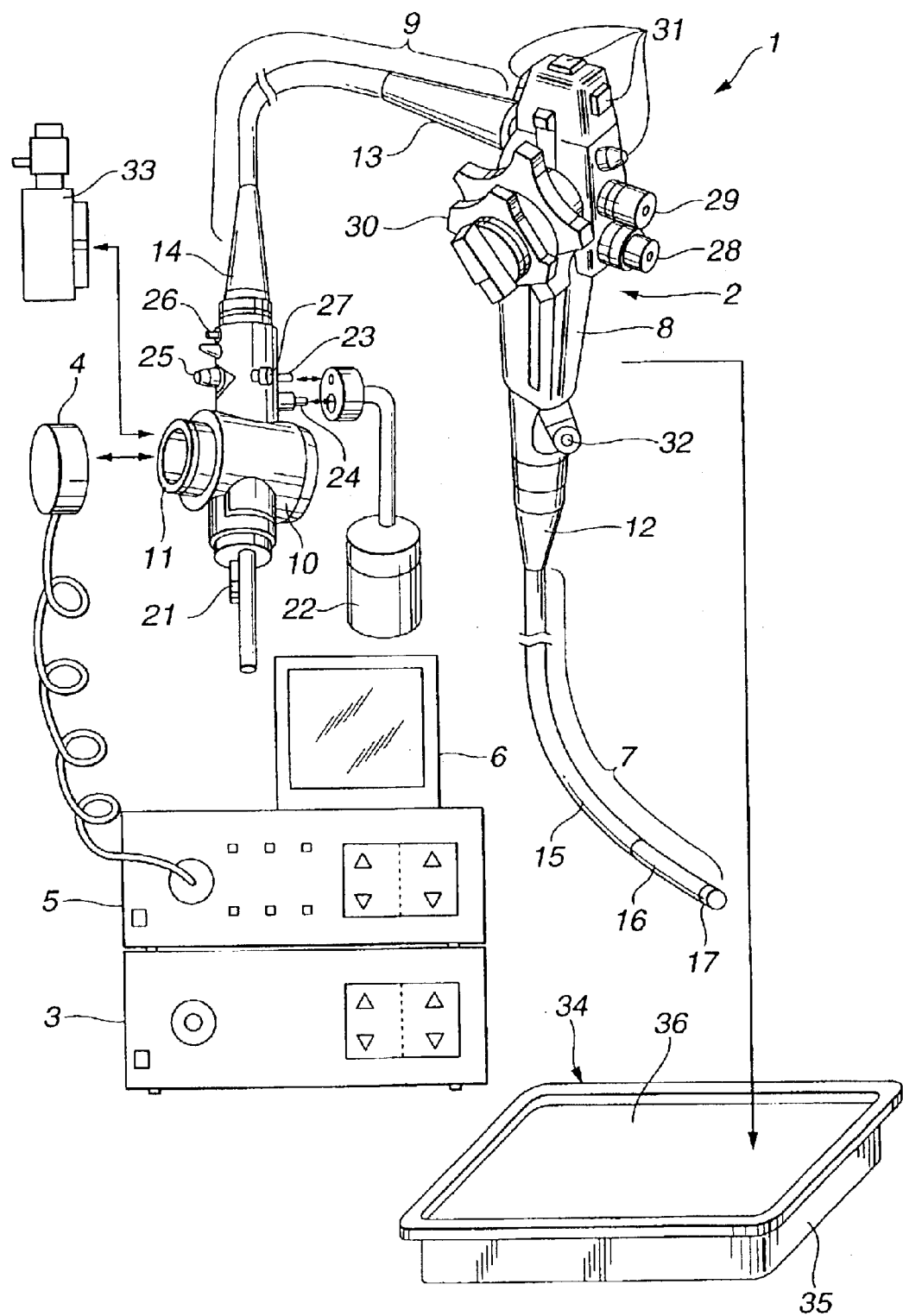

As shown in FIG. 1, an endoscope apparatus 1 is configured to include an endoscope 2 of the first embodiment with built-in image pickup means, a light source device 3 which is freely detachably connected to the endoscope 2 and which supplies illumination light to a light guide (not shown in the drawing) arranged in the endoscope 2, a video processor 5 which is connected to the endoscope 2 via a signal cable 4 and which controls an image pickup means of the endoscope 2 and, in addition, processes signals obtained from the image pickup means, and a monitor 6 for displaying an image corresponding to a subject image output from the video processor 5.

The endoscope 2 is configured such that after the use for observation and therapy, cleaning is performed, and subsequently, sterilization can be performed by high-temperature high-pressure steam sterilization (may be referred to as autoclave sterilization). This endoscope 2 is configured to include a slender insertion portion 7 having flexibility, an operating portion 8 connected to the proximal end part of the insertion portion 7, a flexible connecting code 9 extended from the side portion of the operating portion 8, a connector portion 10 which is arranged at the end portion of the connecting code 9 and which is connected to the aforementioned light source device 3 while being freely attached and detached, and an electric connector portion 11 which is arranged at the side portion of the connector portion 10 and to which the aforementioned signal cable 4 connected to the aforementioned video processor 5 can be connected while being freely attached and detached.

A ventilation portion, although not shown in the drawing, for communication between the inside and the outside of the endoscope 2 is arranged in the electric connector 11.

An insertion portion folding-preventing member 12 including an elastic member for preventing sharp bending of a connection portion is arranged at the connection portion of the insertion portion 7 and the operating portion 8. An operating portion folding-preventing member 13 including a similar elastic member is arranged at the connection portion of the operating portion 8 and the connection cord 9 and, furthermore, a connector portion folding-preventing member 14 including a similar elastic member is arranged at the connection portion of the connection cord 9 and the connector portion 10.

The insertion portion 7 is composed of a soft flexible tube 15 having flexibility, curve portion 16 which is arranged at the distal end of the flexible tube 15 and which can be curved by operation of the operating portion 8, and a tip portion 17 which is arranged at the distal end and which is provided with an observational optical system, illuminational optical system, etc., although not shown in the drawing.

In the tip portion 17, a gas and water supply nozzle, not shown in the drawing, for ejecting a cleaning liquid or gas toward an optical member on the outer surface of the observational optical system, not shown in the drawing, by a gas supply operation or water supply operation and a suction port which is an opening at the distal end of a therapeutic instrument channel, not shown in the drawing, arranged in the insertion portion 7 in order to insert a therapeutic instrument therein and to suction liquid in a body cavity are arranged, individually. A liquid supply port for ejecting the liquid is arranged at the tip portion while being opened toward an observation object.

The connector portion 10 is provided with a gas supply base 21 connected to a gas supply source, not shown in the drawing, built in the light source device 3 while being freely attached and detached and a water supply tank pressurizing base 23 and a liquid supply base 24 connected to a water supply tank 22 as a liquid supply source while being freely attached and detached, individually. A suction base 25 connected to a suction source, not shown in the drawing, for performing suction from the aforementioned suction port is arranged on the side surface of the near side of the connector portion 10. Furthermore, an injection base 26 connected to a water supply device, not shown in the drawing, for performing water supply from the liquid supply port is arranged and, in addition, an earth terminal base 27 for returning leakage current to a diathermic therapy device when high frequency leakage current is generated in the endoscope during performance of diathermic therapy, etc., is arranged in the neighborhood of the suction base 25.

The operating portion 8 is provided with a gas and water supply operation button 28 for operating a gas supply operation and a water supply operation, a suction operation button 29 for performing a suction operation, a curving-operation knob 30 for performing a curving operation of the aforementioned curve portion 16, a plurality of remote switches 31 for remotely controlling the aforementioned video processor 5, and a therapeutic instrument insertion port 32 which is an opening communicated to the aforementioned therapeutic instrument channel (not shown in the drawing), individually.

A waterproof cap 33 with a pressure control valve can be connected to the electric connector portion 11 of the endoscope 2 while being freely attached and detached. This waterproof cap 33 with a pressure control valve is provided with a pressure control valve, not shown in the drawing.

When the aforementioned endoscope apparatus 1 having the aforementioned configuration is subjected to high-temperature high-pressure steam sterilization, a sterilization storage case 34 for storing the aforementioned endoscope 2 is used. This storage case 34 is composed of a tray 35 and a lid member 36.

The tray 35 and the lid member 36 are provided with a plurality of vent holes, not shown in the drawing, and steam can be passed through these holes.

Next, a high-temperature high-pressure steam sterilization treatment for disinfection and sterilization of the aforementioned endoscope 2 will be described. Regarding the typical conditions of the high-temperature high-pressure steam sterilization (autoclave sterilization), in the US standard ANSI/AAMI ST37-1992 approved by American National Standards Institute and issued by Association for the Advancement of Medical Instrumentation, the condition of sterilization step is specified to be at 132° C. for 4 minutes in prevacuum type, and the condition of the sterilization step is specified to be at 132° C. for 10 minutes in gravity type.

Although the temperature condition during the sterilization step of high-temperature high-pressure steam sterilization varies depending on the form of high-temperature high-pressure steam sterilization apparatuses and the time of the sterilization step, in general high-temperature high-pressure steam sterilization, the temperature is set within the range on the order of 115° C. to 138° C. Some sterilization apparatuses can be set at on the order of 142° C.

The time condition varies depending on the temperature condition during the sterilization step. In general, it is set for on the order of 3 minutes to 60 minutes. Some sorts of sterilization apparatuses can be set for on the order of 100 minutes.

The pressure in a sterilization chamber during this step is generally set at on the order of +0.2 MPa relative to atmospheric pressure.

A general high-temperature high-pressure steam sterilization step of the prevacuum type includes a prevacuum step of bringing the inside of the sterilization chamber storing a target apparatus for sterilization into the condition of reduced pressure in advance of the sterilization step and a subsequent sterilization step of supplying high-temperature high-pressure steam into the sterilization chamber so as to perform sterilization.

The prevacuum step is a step for allowing steam to penetrate into detail of the target apparatus for sterilization during the later sterilization step, and by reducing the pressure in the sterilization chamber, high-temperature high-pressure steam goes throughout the target apparatus for sterilization.

In this case, the pressure in the sterilization chamber during this prevacuum step is generally set at on the order of −0.07 MPa to −0.09 MPa relative to atmospheric pressure.

In order to dry the sterilized target apparatus after sterilization, the aforementioned high-temperature high-pressure steam sterilization step of the prevacuum type may include a drying step of bringing the inside of the sterilization chamber into the condition of reduced pressure again after the sterilization step. In this step, the pressure in the sterilization chamber is reduced so as to remove steam from the sterilization chamber and, therefore, drying of the sterilized target apparatus in the sterilization chamber is accelerated. In general, the pressure in the sterilization chamber during this step is set at on the order of −0.07 to −0.09 MPa relative to atmospheric pressure.

Next, a treatment method for performing such a high-temperature high-pressure steam sterilization step will be described.

The endoscope 2 is assumed to be subjected to the high-temperature high-pressure steam sterilization. In this case, the endoscope 2 is in the condition that the waterproof cap 33 with a pressure control valve is mounted to the electric connector portion 11. Under this condition, the pressure control valve, not shown in the drawing, of the aforementioned waterproof cap 33 with a pressure control valve is closed, the aforementioned vent holes are blocked by the waterproof cap 33 with a pressure control valve and, therefore, the inside of the endoscope 2 is in the condition of being sealed watertight from the outside.

In the case where the sterilization method including the prevacuum step is performed, when the pressure in the sterilization chamber in use is reduced and the pressure difference in which the external pressure becomes lower than the internal pressure of the endoscope 2 is generated during the prevacuum step, the pressure control valve of the aforementioned waterproof cap 33 with a pressure control valve is opened and, therefore, the inside of the endoscope 2 and the outside are brought into communication via the aforementioned vent holes therebetween. Consequently, occurrence of a large pressure difference between the pressure inside the endoscope 2 and the pressure inside the sterilization chamber is prevented. According to this, the endoscope 2 is prevented from being broken due to the pressure difference between the inside and the outside.

In the sterilization step, when the inside of the sterilization chamber is pressurized and the internal pressure and the external pressure of the endoscope 2 become nearly equivalent, the pressure control valve of the aforementioned waterproof cap 33 with a pressure control valve is closed. According to this, the high-pressure high-temperature steam does not actively enter into the inside of the endoscope 2 from the route through which the aforementioned waterproof cap 33 with a pressure control valve and the aforementioned vent holes are communicated.

However, the high-pressure steam may gradually enter into the inside through the integument of the aforementioned flexible tube formed from a macromolecular material, or through the O-ring which is a seal device arranged at the connection portion of the outer sheath material of the endoscope 2 and which is formed from fluororubber, silicon rubber, etc., and the like.

In this case, the outer sheath material of the endoscope 2 becomes in the state that a pressure has been generated, wherein the pressure decreased in the prevacuum step and the pressure increased in the sterilization step are added and the resulting pressure trends from the outside toward the inside.

In the case where the method includes a pressure reduction step after the sterilization step, in the pressure reduction step, the pressure in the sterilization chamber is reduced, the external pressure becomes lower than the internal pressure of the endoscope 2 so that the pressure difference is generated and, at nearly the same time, the pressure control valve of the aforementioned waterproof cap 33 with a pressure control valve is opened so that the inside of the endoscope 2 and the outside become in the condition of being communicated via the aforementioned vent holes therebetween. Consequently, occurrence of a large pressure difference between the pressure inside the endoscope 2 and the pressure in the sterilization chamber is prevented. According to this, the endoscope 2 is prevented from being broken due to the pressure difference between the inside and the outside.

When the pressure difference between the inside and the outside of the endoscope 2 is eliminated because of the aforementioned actions, the pressure control valve of the aforementioned waterproof cap 33 with a pressure control valve is closed.

When all steps of the high-temperature high-pressure steam sterilization treatment are completed as described above, the outer sheath material of the endoscope 2 becomes in the condition that a pressure, which corresponds the pressure reduced in the pressure reduction step and which trends from the outside toward the inside, has been generated.

Thereafter, when the aforementioned waterproof cap 33 with a pressure control valve is removed from the electric connector portion 11, the inside of the endoscope 2 and the outside are communicated through the aforementioned vent holes and, therefore, the inside of the endoscope 2 becomes at atmospheric pressure, and the load due to the pressure which has been applied to the outer sheath material of the endoscope 2 is eliminated.

Next, the endoscope 2 of the first embodiment will be described in detail.

Figure 2:
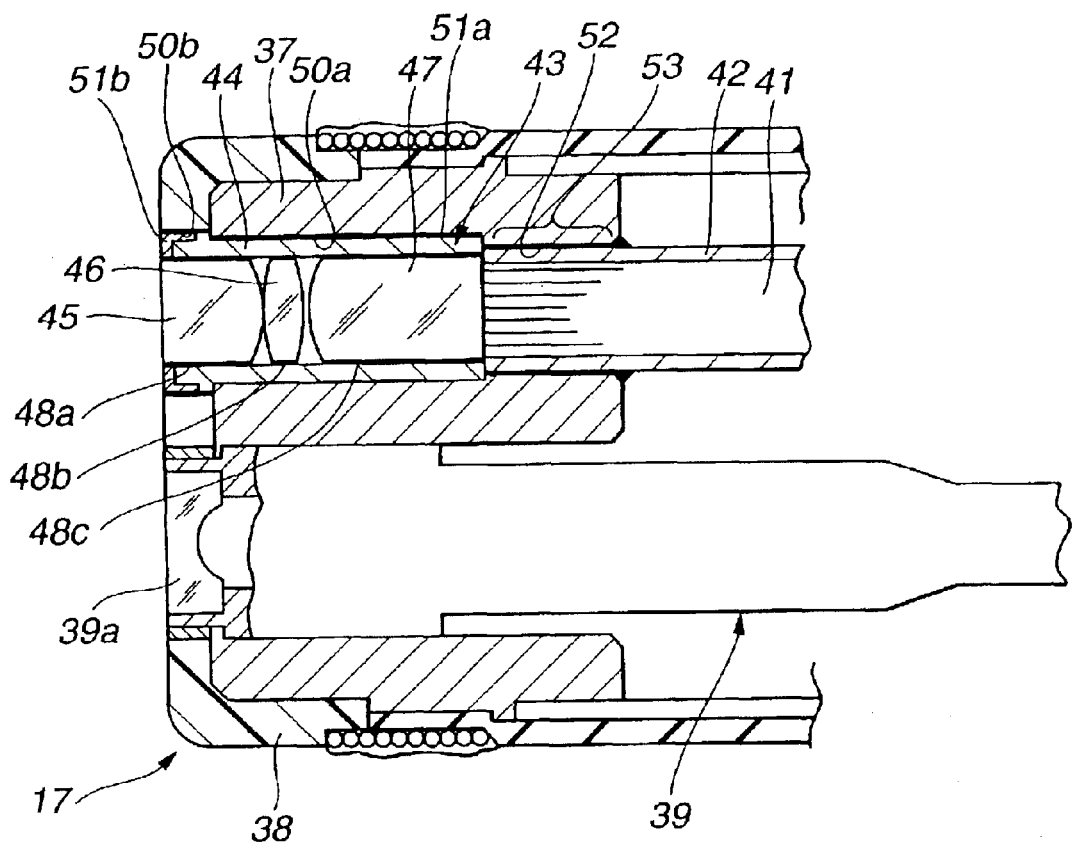

As shown in FIG. 2, the tip hard portion constituting the tip portion 17 of the endoscope 2 of the present embodiment is provided with: an objective front lens (hereafter abbreviated as tip lens) 39a and an objective back lens group 39c constituting an observational optical system (objective optical system) 39s; the observational optical system unit (or image pickup unit) 39 composed of a charge-coupled device (hereafter abbreviated as CCD) 39i as a solid image pickup element on which a subject image is formed by the observational optical system 39s and a cable 39j (refer to FIG. 3), etc.; and an illuminational optical system unit 43 configured by arranging a tip portion illumination lens 45 constituting the illuminational optical system for illuminating the subject observed with the aforementioned observational optical system 39s, an illumination lens 46, and a back side illumination lens 47 in a lens frame 44.

The observational optical system unit 39 will be described.

Figure 3:
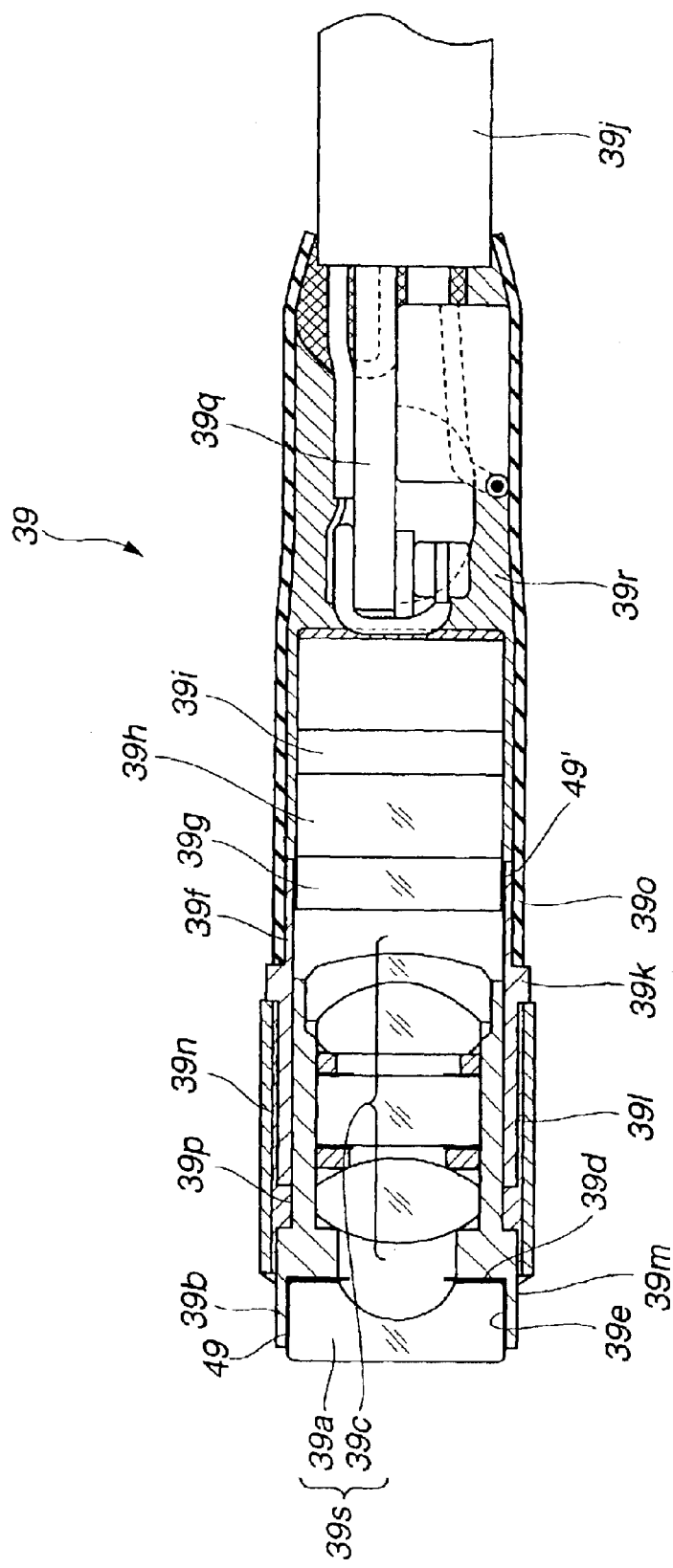

As shown in FIG. 3, the tip lens 39a arranged at the front of the observational optical system unit 39 and exposed to the outer surface is formed from, for example, sapphire or glass having high-temperature steam resistance, and is connected airtight to the cylindrical objective lens frame 39b made of a metal.

A plurality of lens members constituting the observational optical system 39s are nearly fitted into, and mounted on this objective lens frame 39b. At that time, as described later, a surface treatment layer 49 (refer to FIG. 5B) made of a metal is applied to the outer perimeter surface of the aforementioned tip lens 39a mounted to the opening of the front end of this objective lens frame 39b while the front thereof is exposed to the outside, and is joined (sealed) steam-tight to the objective lens frame 39b.

Likewise, a cover glass 39g mounted to the back end of the cover glass frame 39f connected airtight to this objective lens frame 39b as described later has a similar structure, and is joined airtight to the cover glass frame 39f. As described above, a steam-tight structure is established and, thereby, entering of steam inside the observational optical system 39s is prevented even when the observational optical system 39s is subjected to a high-temperature high-pressure steam sterilization treatment.

The aforementioned objective lens frame 39b is formed from a material, for example, SUS304 and SUS304L, which contains less components (phosphorous, sulfur, carbon, etc.) likely to cause cracks due to heat. Regarding the surface of this objective lens frame 39b, for example, an electroplating treatment with nickel is applied to the lower layer, and an electroplating treatment with gold is applied to the outermost layer. The film thickness of nickel is 2 to 4 µm, and that of gold is 0.3 to 0.5 µm, for example.

Regarding the rear side of the tip lens 39a, the aforementioned objective back lens group 39c is mounted to the objective lens frame 39b and is fixed. A diaphragm 39d is put into this objective lens frame 39b and, thereafter, the objective front lens 39a is fitted into the frame.

The gap between the inner diameter of the objective lens frame 39b and the outer diameter of the tip lens 39a in a fitted portion 39e, where this tip lens 39a is fitted, is minimized and is set based on mountability and a processing tolerance limit. Furthermore, the thickness of the fitted portion 39e of the objective lens frame 39b is minimized.

The cover glass 39g formed from, for example, sapphire or glass having high-temperature steam resistance, is arranged on the back end side of the objective back lens group 39c, and this cover glass 39g is connected airtight to the cover glass frame 39f made of a metal.

A surface treatment layer 49', as described later, similar to that of the aforementioned tip lens 39a is applied to the outer perimeter surface of the cover glass 39g.

The cover glass frame 39f is formed from SUS304, SUS304L, etc., similarly to the aforementioned objective lens frame 39b.

The front surface of an infrared ray removing filter 39h for cutting infrared rays is closely bonded to the rear surface of the cover glass 39g, and the front surface of the aforementioned CCD 39i is bonded and fixed to the rear surface of this infrared ray removing filter 39h while being in the close contact condition with being optical-axis adjusted by a reticle, etc. The rear surface of this CCD 39i is provided with a substrate 39q equipped with electronic components, for example, an integrated circuit (abbreviated as IC) and capacitor, and the circumference thereof is sealed with an adhesive having insulation property.

The CCD 39i or substrate 39q is electrically connected to the cable 39j. This cable 39j is connected to an electric contact of the electric connector portion 11 shown in FIG. 1, and is connected to the video processor 5 through the signal cable 4 connected to this electric connector portion 11.

The observational optical system 39s shown in FIG. 3 does not include cover glass 39g. However, the cover glass 39g may be included. The cover glass 39g may have a function as a lens.

FIG. 3 shows the structure in which the infrared ray removing filter 39h is in close contact with the rear surface of the cover glass 39g, and the front surface of the CCD 39i is in close contact with the rear thereof. However, this infrared ray removing filter 39h may be arranged between the objective back lens group 39c and the cover glass 39g, and the front surface of the CCD 39i may be directly adhered to the rear surface of the cover glass 39g.

The back end side of the objective lens frame 39b is fitted to the cover glass frame 39f and is moved in the direction of the optical axis. Consequently, adjustment of the focus of the observational optical system 39s and the image pickup surface of the CCD 39i can be performed by the tip lens 39a and the objective back lens group 39c. After this adjustment of the focus is performed, the aforementioned objective lens frame 39b and the aforementioned cover glass frame 39f are fixed airtight as described later.

A stopper 39k is arranged on the outer perimeter surface of the cover glass frame 39f, and the outer diameter of the outer perimeter surface 39l located nearer to the tip than is this stopper 39k and the outer diameter of the maximum outer diameter portion 39m of the aforementioned objective lens frame 39b are nearly the same.

A hollow cylindrical member 39n is fitted between the outer perimeter surface 39l located nearer to the tip than is this stopper 39k and the maximum outer diameter portion 39m of the objective lens frame 39b while being in contact with the aforementioned stopper 39k.

The inner diameter of this cylindrical member 39n is formed to be larger than the outer diameters of the aforementioned maximum outer diameter portion 39m of the objective lens frame 39b and the tip side outer perimeter surface 39l of the aforementioned cover glass frame 39f by about 0.1 mm, for example.

A solder layer 39p is formed by pouring solder into the gaps between the objective lens frame 39b and the cylindrical member 39n and between the cover glass frame 39f and the cylindrical member 39n and, thereby, these are configured to be joined airtight, individually. That is, the objective lens frame 39b and the cover glass frame 39f are connected and fixed in order that the joint portion thereof becomes airtight.

The back side of the cover glass frame 39f, from the outer perimeter portion on the back side of the aforementioned stopper 39k to the tip end portion of the cable 39j, is covered with a heat-shrinkable tube 39o, and the inside of the heat-shrinkable tube 39o is filled with, for example, an epoxy-based adhesive 39r.

Next, a structure and an assembling method in which the tip lens 39a is fitted into the objective lens frame 39b and is joined airtight will be described.

The surface treatment layer 49 applied to the outer perimeter surface of the tip lens 39a will be described.

Figure 5A:
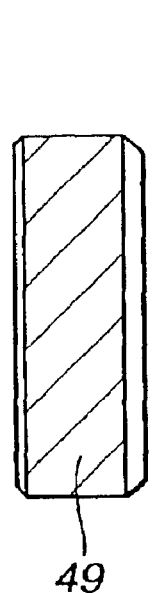
FIG. 5A is a side view showing the tip lens.
Figure 5B:
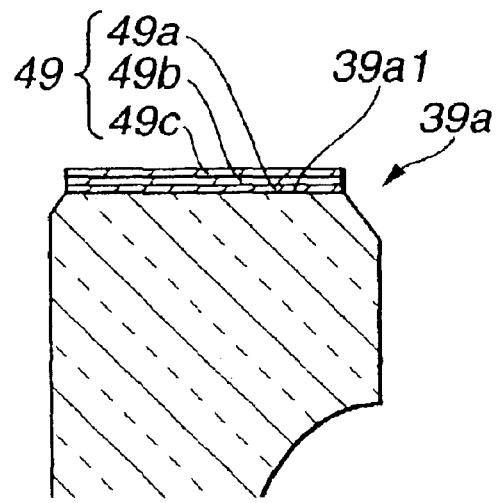

As shown in FIG. 5A, the surface treatment layer 49 is formed on the outer perimeter surface of the tip lens 39a. That is, as shown in FIG. 5B, the surface treatment layer 49 is formed on the circular-ring-shaped outer perimeter surface 39a1 of the tip lens 39a.

This surface treatment layer 49 is composed of the lowermost (innermost) layer 49a, intermediate layer 49b in between, and outermost layer 49c.

That is, the lowermost layer 49a at the bottom of the tip lens 39a is formed from a chromium film having high adherence to sapphire and glass constituting this tip lens 39a.

The lowermost layer 49a formed from the chromium film is formed by evaporation in vacuum or sputtering in vacuum.

The intermediate layer 49b is formed from a nickel layer. The outermost layer 49c is formed from a gold layer. This gold layer may be formed by evaporation in vacuum or sputtering in vacuum. However, an electroplating treatment by electroplating can make the film thickness larger. The tip lens 39a thus subjected to the surface treatment is fitted into the objective lens frame 39b as shown in FIG. 4 and is joined airtight.

Figure 4:
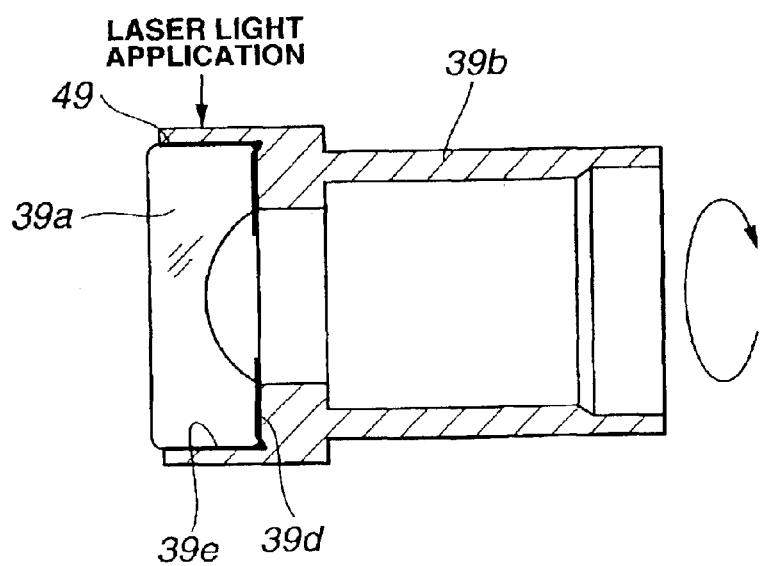

The aforementioned diaphragm 39d and the tip lens 39a are dropped into the objective lens frame 39b, and laser light is applied to the outer perimeter surface of the fitted portion 39e of the objective lens frame 39b fitted with the tip lens 39a from the direction indicated by an arrow shown in FIG. 4 by a laser apparatus, not shown in the drawing. This laser apparatus, for example, uses a YAG laser capable of performing fine adjustment at a low output.

By this laser light, gold constituting the outermost layer 49c of the surface treatment layer 49 arranged on the outer perimeter surface 39a1 of the tip lens 39a and gold of the outermost layer of the objective lens frame 39b are individually fused and cooled so as to join.

This laser light application is performed all over the perimeter of the objective lens frame 39b. In order to perform this, the objective lens frame 39b may be rotated as indicated by an arrow shown in FIG. 4.

When the application is performed with a pulsed-wave laser, airtightness can be ensured with reliability by allowing the overlap with the adjacent pulse to become 80% or more. According to this, the tip lens 39a and the objective lens frame 39b can be joined while airtightness is ensured.

Next, a structure and an assembling method in which the cover glass 39g is fitted into the cover glass frame 39f and is joined airtight will be described. Initially, the surface treatment layer 49' applied to the cover glass 39g (refer to FIG. 3) will be described.

The outer perimeter surface of this cover glass 39g is provided with the surface treatment layer 49' (refer to FIG. 3) similar to the surface treatment layer 49 of the tip lens 39a shown in FIG. 5B. As the bottom layer (metallized layer), a chromium film having high adherence to sapphire and glass is formed. The chromium film is formed by evaporation in vacuum or sputtering in vacuum.

An opaque mask is formed on the periphery of the plane portion of this cover glass 39g by vacuum evaporation or sputtering. By this mask, entering of unnecessary light into the CCD 39i side is prevented. This mask may be formed by a three-layer step of, for example, chromium oxide-chromium-chromium oxide.

The lowermost layer of the surface treatment layer 49' may be formed by the same treatment as that of the formation of this mask.

That is, the lowermost layer of the surface treatment layer 49' may be formed by performing the three-layer step of chromium oxide-chromium-chromium oxide, furthermore, a nickel layer may be formed as the intermediate layer and, finally, a gold layer may be formed as the outermost layer. The gold layer may be formed by evaporation in vacuum or sputtering in vacuum. However, an electroplating treatment by electroplating can make the film thickness larger.

The cover glass 39g thus provided with the surface treatment layer 49' is fitted into the cover glass frame 39f and is joined airtight.

The aforementioned cover glass 39g is dropped into the cover glass frame 39f, and is positioned by a jig, not shown in the drawing. Laser light is applied to the outer perimeter surface of the fitted portion (not shown in the drawing) of the cover glass frame 39f fitted with this cover glass 39g by a laser apparatus, not shown in the drawing.

By the laser light application, gold of the outer perimeter surface of the cover glass 39g and gold of the outermost layer of the cover glass frame 39f are individually fused and cooled and, therefore, the gold of the outer perimeter surface of the cover glass 39g and the gold of the outermost layer of the cover glass frame 39f are joined. This laser light application is performed all over the perimeter of the cover glass frame 39f.

According to this, the cover glass 39g and the cover glass frame 39f can be joined while airtightness is ensured.

The objective lens frame 39b joined airtight to the aforementioned tip lens 39a and the cover glass frame 39f joined airtight to the aforementioned cover glass 39g are joined airtight to the cylindrical member 39n, respectively.

The objective lens frame 39b and the cover glass frame 39f are fitted to each other, and are bonded after adjustment of the focus. Required portions are coated with flux and ring-shaped solder fills upto the stopper 39k. Subsequently, the cylindrical member 39n is dropped into.

Local heating is performed with respect to the stopper 39k by, f or example, high frequency waves while a load is applied to the cylindrical member 39n and, therefore, the solder is fused. Since gaps are filled with the solder because of the surface tension, the gaps between the objective lens frame 39b and the cylindrical member 39n and between the cover glass frame 39f and the cylindrical member 39n are filled, respectively, and therefore, the solder layer 39p is formed. According to this, the inside of each frame can be joined and kept airtight.

Consequently, according to the aforementioned configuration, the joint portion of the observational optical system unit 39 is joined while being sealed steam-tight.

Next, the illuminational optical system will be described. As shown in FIG. 2, the tip portion of a light guide 41 is fixed to a light guide base 42. An illuminational optical system unit 43 is arranged at the tip side of this light guide base 42.

The illuminational optical system unit 43 is composed of an illumination lens frame 44, and a tip side illumination lens 45, illumination lens 46, and back side illumination lens 47 which are arranged in this illumination lens frame 44.

The fitted portions of the outer perimeters of the tip side illumination lens 45, illumination lens 46, and back side illumination lens 47 with the illumination lens frame 44 are provided with bonding portions 48a, 48b, and 48c. These bonding portions 48a, 48b, and 48c join and fix the outer perimeter surfaces of the tip side illumination lens 45, illumination lens 46, and back side illumination lens 47, respectively, to the inner side of the illumination lens frame 44 with an adhesive containing an epoxy resin, etc., as a base. In this case, at least the bonding portions 48a and 48c seal the illumination lens frame 44 and each of the lenses 45 and 48 not with steam-tightness, but with liquid-tightness.

The illuminational optical system unit 43 is fitted into an illuminational optical system unit mounting hole 50a of a hard tip constituent 37 and into a mounting hole 50b of an insulation cover member 38.

The fitted portions of the illuminational optical system unit mounting hole 50a and the mounting hole 50b of the insulation cover member 38 to the illuminational optical system unit 43 are provided with bonding portions 51a and 51b. These bonding portions 51a and 51b join and fix the outer perimeter portion of the illuminational optical system unit 43 to the illuminational optical system unit mounting hole 50a and the mounting hole 50b of the insulation cover member 38 with an adhesive containing an epoxy resin, etc., as a base. In this case, the bonding portions 51a and 51b of the joint portions perform sealing not with steam-tightness, but with liquid-tightness.

On the other hand, the light guide base 42 arranged at the back end side of the illuminational optical system unit 43 is fitted into a light guide mounting hole 52 of the tip constituent 37. This light guide base 42 is fixed to the tip constituent 37 with a screw, etc., not shown in the drawing.

The fitted portion 53 of the light guide base 42 and the aforementioned light guide mounting hole 52 is coated with a filler containing silicon, etc., as a base and, therefore, is configured to avoid entering of dust, etc., into the contact portion between the back side illumination lens 47 and the light guide 41, from the base end portion side in FIG. 2 via the fitted portion 53.

The front portion of the outer perimeter surface of the tip constituent 37 is covered with the insulation cover member 38, the most distal end of the curved piece constituting the curve portion 16 is fixed to the back end side portion, and the outer perimeter side thereof is covered with a rubber tube.

In the configuration of the present embodiment, as described above, the layer made of gold or a gold alloy is formed on the joint surface of the lens member of the observational optical system 39s and the frame member made of a metal, this layer is fused by laser light application so as to join them and, therefore, the junction keeps steam-tightness, while the joint portion of the lens member of the illuminational optical system and the frame member made of a metal is joined with an adhesive and, therefore, the junction keeps liquid-tightness.

Put another way, the illuminational optical system side has a low level of steam-tight structure in which steam enters during the high-temperature high-pressure steam sterilization. In this case, although steam enters during the high-temperature high-pressure steam sterilization, since heat is generated in the illuminational optical system portion accompanying the illumination light during the endoscope inspection, the steam entered inside the illuminational optical system can be discharged by the heat. Consequently, even the low level of steam-tight structure can reduce the influence exerted on the illuminational optical system and, thereby, merits are brought about in that the cost reduction can be achieved, and repair can be further simplified.

That is, in the configuration of the present embodiment, the steam-tight level of the joint portion of the lens member of the illuminational optical system and the frame member fitted with the lens member is allowed to be lower than the steam-tight level of the joint portion of the lens member of the observational optical system 39s and the frame member fitted with the lens member.

Regarding the steam-tight level of the joint portion in the observational optical system, the pressure resistance for preventing entering of steam is specified to be about 0.2 Mpa or more with respect to at least the joint portion where the internal space of the observational optical system is distinguished from the external space of the endoscope. Here, 0.2 Mpa is a maximum pressure applied during the sterilization step of common high-temperature high-pressure steam sterilization.

On the other hand, regarding the steam-tight level of the joint portion in the illuminational optical system, the pressure resistance for preventing entering of liquid is specified to be about 0.05 Mpa or more with respect to at least the joint portion where the internal space of the illuminational optical system is distinguished from the external space of the endoscope. However, it is formed to be at such level that steam enters at a pressure, for example, on the order of 0.1 Mpa to 0.2 Mpa.

Here, 0.05 Mpa is the guaranteed pressure resistance to entering of the liquid with respect to all joint portions of the outer surface of a common endoscope. This pressure is the pressure with which entering of the liquid can be prevented with respect to the liquid pressure during immersion in water or a chemical solution in cleaning operation or disinfection operation, or treatment in a common automatic cleaning disinfector, etc.

Next, the actions of the present embodiment will be described.

In the present embodiment, the endoscope 2 is assumed to be subjected to high-temperature high-pressure steam sterilization. In this case, even when the endoscope 2 is exposed to high-pressure steam, since all outside junctions of the aforementioned observational optical system unit 39 are joined while being sealed at a steam-tight level, steam does not enter into the observational optical system unit 39. According to this, observation is not affected by fogging of the lens. That is, stabilized observation performance can be exerted. The expensive observational optical system unit 39 becomes unlikely to break and, as a result, durability of the endoscope 2 can be improved.

On the other hand, although the seal levels of the bonding portions 48a and 51b of the illuminational optical system unit 43 are liquid-tight, since these are not steam-tight at a pressure of 0.2 Mpa, some quantities of steam may enter inside the illuminational optical system unit 43. Furthermore, since the seal levels of other bonding portion Sla and the fitted portion 53 are not steam-tight, some quantities of steam may enter between the illuminational optical system unit 43 and the light guide 41.

Consequently, when the tip portion 17 is cooled with cool water after high-temperature high-pressure steam sterilization and when water is supplied from a gas and water supply nozzle 18 (refer to FIG. 6) by operation of the gas and water supply operation button 28 during inspection and, therefore, the illuminational optical system unit 43 is cooled, moisture in the illuminational optical system unit 43 condenses, so that fogging of these lenses may occur. However, the loss of illumination light due to this fogging is on the order of 10% even at the maximum.

When inspection is started, even if fogging occurs, since individual members and spaces are heated by the illumination light supplied from the light guide 41, the condensation is eliminated and the fogging disappears. Furthermore, the time of occurrence of the fogging is on the order of several seconds. Therefore, it is almost insignificant in practical use.

When automatic light control is performed, light from the light source device 3 is appropriately adjusted and the quantity of light supply is increased. Consequently, there is no problem in practical use.

By supplying illumination light during inspection, moisture is dried when the inspection is completed and, therefore, entered steam is hardly accumulated.

In the present embodiment, regarding the seal of the illuminational optical system, soldering, brazing, laser welding, and steam-tight junction by an adhesive, in which very expensive adhesive is required for ensuring steam-tightness and there are restrictions with respect to the length of the bonding portion and the clearance, are not performed, but the seal property is specified to be at a liquid-tight level by using common bonding, etc. Consequently, the material cost and assembly cost of the endoscope 2 itself are reduced. Disassembly thereof is performed with ease, and repair is performed with ease.

The present embodiment has the following effect.

According to the present embodiment, an inexpensive endoscope in which observation performance is not degraded even when high-temperature high-pressure steam sterilization is performed and which has excellent repairability can be realized.

(Second Embodiment)

The second embodiment of the present invention will be described with reference to FIG. 6.

Initially, the configuration of the present embodiment will be described. The overall configuration of an endoscope of the present embodiment is similar to that shown in FIG. 1. FIG. 6 shows the configuration of the tip portion of the endoscope according to the second embodiment.

Although when the tip portion 17 is cooled with cool water after high-temperature high-pressure steam sterilization and when water is supplied from a gas and water supply nozzle 18 (refer to FIG. 6) by operation of the gas and water supply operation button 28 during inspection and, therefore, the illuminational optical system unit 43 is cooled, moisture in the illuminational optical system unit 43 may condense and fogging of these lenses may occur, regarding the endoscope of the present embodiment, occurrence of such fogging is prevented by arranging the water supply nozzle such that the tip lens member of the illuminational optical system is not included within the range of water supplied from the water supply nozzle.

Figure 6:
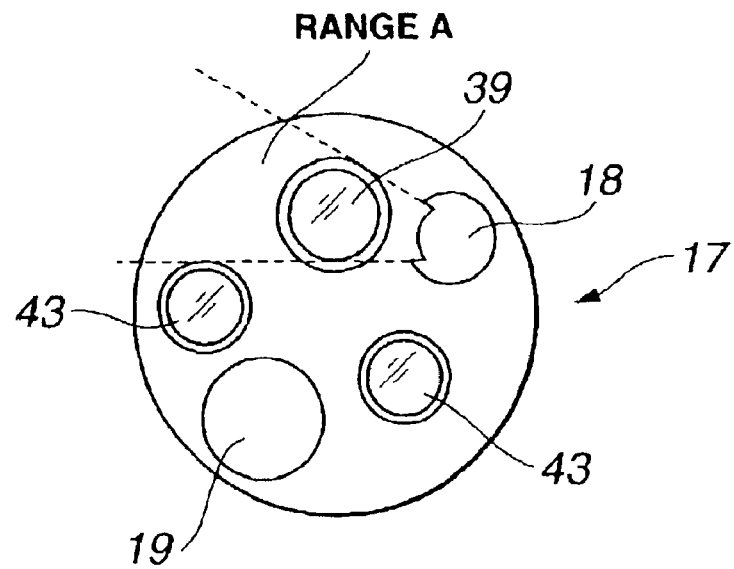
FIG. 6 is a front view showing the configuration of the tip portion of the endoscope according to the second embodiment of the present invention.

As shown in FIG. 6, regarding the tip surface of the tip portion 17, the range A shown in the drawing indicates the water supply range when an operation of supplying water from the gas and water supply nozzle 18 is performed by operation of the gas and water supply operation button 28.

The water ejected from the gas and water supply nozzle 18 is supplied in the range A on the tip surface of the tip portion 17. That is, regarding the configuration on the tip surface of the tip portion 17, the positions of the illuminational optical system unit 43 and the gas and water supply nozzle 18 are positioned such that the illuminational optical system unit 43 is not included within the region of the range A.

Other overall configuration of the endoscope 2 is similar to that in the aforementioned first embodiment.

Next, the actions of the present embodiment will be described.

In the present embodiment, it is assumed that the tip side lens of the illuminational optical system unit 43 has been soiled with filth, mucus, etc., and an operation of supplying water from the gas and water supply nozzle 18 is performed by operation of the gas and water supply operation button 28 in order to remove this.

In this case, since the illuminational optical system unit 43 is arranged in order to avoid entering into the water supply range (range A) of the water supply nozzle 18 on the tip surface of the tip portion 17, the supplied water hardly hits directly the illuminational optical system unit 43. Consequently, the illumination lens frame 44 and the tip side illumination lens 45 are not cooled rapidly by the water supplied.

According to this, condensation of moisture in the gaps between the illumination lens frame 44, illumination lens 46, and back side illumination lens 47 can be reduced, occurrence of significant fogging of them can be prevented and, therefore, occurrence of fogging on a water supply operation basis can be prevented.

Other actions are similar to those in the aforementioned first embodiment.

The present embodiment has the following effect.

According to the present embodiment, in addition to the effects in the aforementioned first embodiment, occurrence of fogging on a water supply operation basis can be prevented. Consequently, an endoscope in which fogging does not occur and which has excellent illumination performance can be realized.

As the junction method for the observational optical system unit 43, the embodiment by laser welding is shown. However, this may be steam-tight junction in which a solderable metallized layer made of a metal film may be formed on the lens side, and this metallized layer and a frame member made of a metal may be brought into metal-junction by solder. The steam-tight junction by an adhesive may also be performed. In such a case, effects similar to those in the aforementioned embodiment can also be achieved.

(Third Embodiment)

The configuration of the present embodiment will be described.

Figure 7:
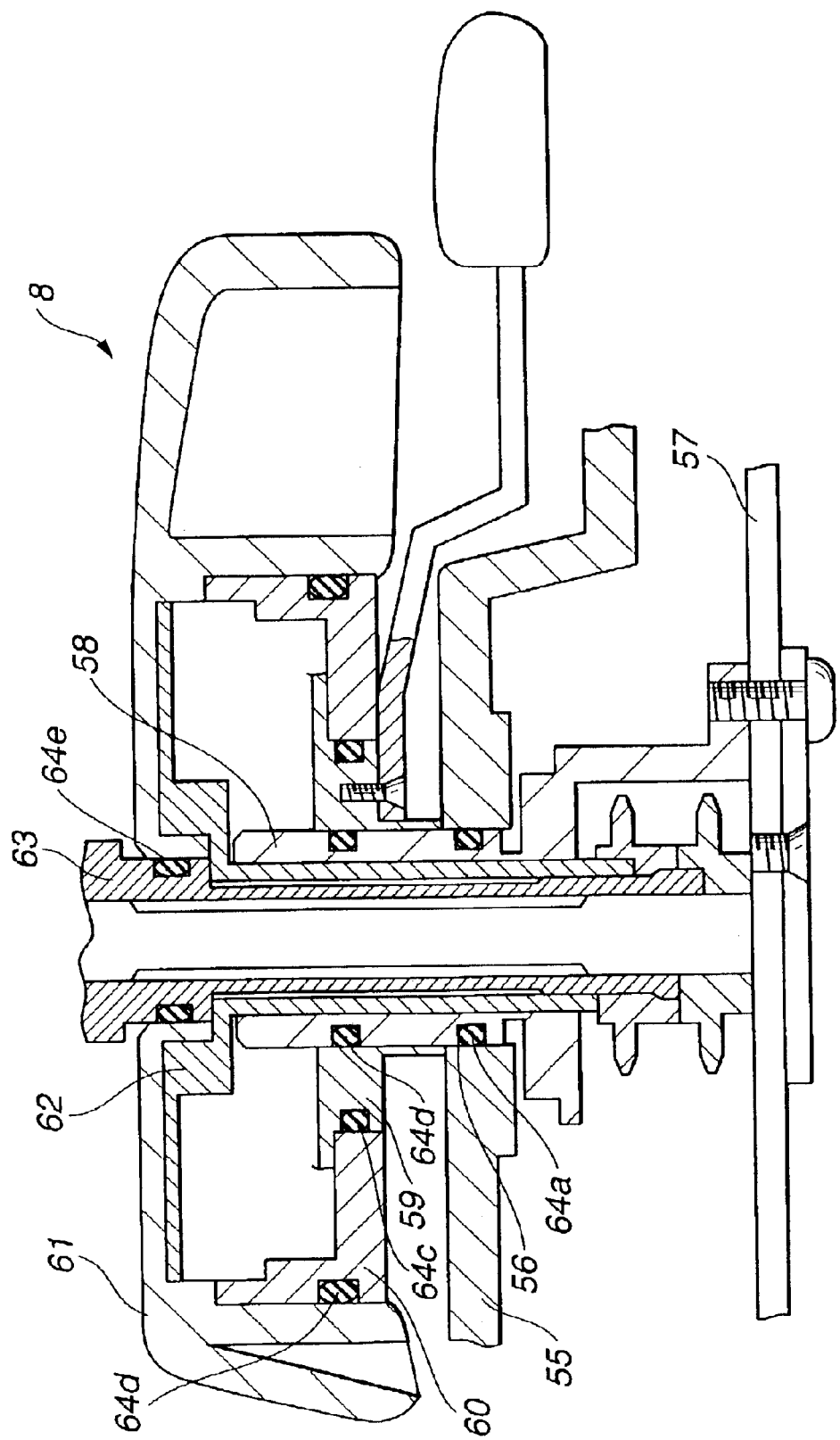
FIG. 7 is a sectional view showing the configuration of a curving-operation knob of an operating portion in the third embodiment of the present invention.

FIG. 7 is a sectional view showing the configuration of a curving-operation knob of an operating portion in the third embodiment of the present invention.

Regarding an endoscope of the present embodiment, in order to improve operability of the operating portion, the sealing member of the movable portion is formed from a material having a steam permeability that is lower than the steam permeability of a resin constituting the integument of the flexible tube of the insertion portion.

As shown in FIG. 7, a fixed axis 58 is fitted into a penetration hole 56 of an operating portion casing 55 of the operating portion 8. This fixed axis 58 is arranged in the operating portion 8, and is fixed to an operating portion chassis 57 fixed to the operating portion 8.

An O-ring 64a as a sealing member is arranged between the penetration hole 56 and the fixed axis 58.

A curving-knob braking operation axis 59 is rotatably fitted outside the fixed axis 58. This curving-knob braking operation axis 59 is connected to a brake mechanism, not shown in the drawing, built in a curving-knob body casing 61.

An O-ring 64b as a sealing member is arranged between the fixed axis 58 and the curving-knob braking operation axis 59.

A curving-operation knob bottom casing 60 is rotatably fitted outside the curving-knob braking operation axis 59 relative to the curving-knob braking operation axis 59. An O-ring 64c as a sealing member is arranged between this curving-knob braking operation axis 59 and the curving-operation knob bottom casing 60.

The curving-operation knob body casing 61 is fitted outside the curving-operation knob bottom casing 60, and is unrotatingly fixed to the curving-operation knob bottom casing 60 by a means of adhesion, etc. An O-ring 64d as a sealing member is arranged between this curving-operation knob bottom casing 60 and the curving-operation knob body casing 61.

A first curving-operation axis 62 fixed unrotatingly to the curving-operation knob body casing 61 is rotatably fitted into the fixed axis 58 relative to the fixed axis 58.

A second curving-operation axis 63 is fitted rotatably into the first curving-operation axis 62 and the curving-operation knob body casing 61 relative to the first curving-operation axis 62 and the curving-operation knob body casing 61.

An O-ring 64e as a sealing member is arranged between the curving-operation knob body casing 61 and the second curving-operation axis 63.

In the configuration of the present embodiment, the O-rings 64a and 64d as sealing members inserted into the fixed portions and the O-rings arranged at the joint portions of the other fixed portions in the outer sheath of the endoscope 2 are formed from a material, for example, fluororubber, having poor steam permeability and a material having high hardness, and the squeeze ratio is made high in order that steam becomes extremely unlikely to pass through.

On the other hand, the O-rings 64b, 64c, and 64e as sealing members inserted into the movable portions and the O-rings arranged at the joint portions of the other rotary portions in the outer sheath of the endoscope 2 are formed from a material, for example, silicon rubber, having excellent steam permeability, but low hardness, so that the squeeze ratio is made suitable for operation performance. According to such a configuration, the operation performance of the movable portion is allowed to be a proper quantity of force.

Other configuration is similar to that in the aforementioned first embodiment.

Regarding the material of the O-ring arranged in the movable portion, the material having a quantity of steam permeation on a unit time basis which is lower than the quantity of steam permeation on a unit time basis of the resin material constituting the integument of the flexible tube 15 of the insertion portion 7.

Regarding the O-ring arranged in the movable portion, when the material, hardness, and squeeze ratio are set in order to have the operation performance equivalent to that of the conventional endoscope not adaptable to high-temperature high-pressure steam sterilization, the surgeon does not have uncomfortable feeling in operation, and the operability becomes excellent.

Next, the actions of the present embodiment will be described.

In the present embodiment, since the O-rings 64b, 64c, and 64e as sealing members inserted into the movable portions and the O-rings arranged at the joint portions of the other rotary portions in the outer sheath of the endoscope 2 are formed from a material, for example, silicon rubber, having excellent steam permeability, but low hardness, and are formed such that the squeeze ratio is made to be suitable for operation performance, the movable portion of the endoscope 2 can be operated with a small quantity of force, and has excellent operability.

Since the quantity of steam permeation from this sealing portion is set to be smaller than the quantity of steam permeation of the resin constituting the flexible tube 15 occupying most of the surface area of the outer sheath of the endoscope 2, the quantity of steam permeation inside the endoscope 2 is hardly changed from the viewpoint of the total endoscope 2.

On the other hand, the quantity of steam permeation from the sealing portion of the fixed portion in the outer sheath of the endoscope 2 is hardly identified.

According to such actions, entering of steam into the endoscope 2 during high-temperature high-pressure steam sterilization can be minimized without sacrificing operability.

The present embodiment has the following effect.

According to the present embodiment, effects similar to those in the aforementioned first embodiment can be achieved and, in addition to this, an endoscope which has excellent operability and in which degradation due to steam of high-temperature high-pressure steam sterilization can be realized.

(Fourth Embodiment)

The fourth embodiment of the present invention will be described with reference to FIG. 8 to FIG. 11. Initially, the configuration of the present embodiment will be described.

An endoscope of the present embodiment is configured in order that steam is unlikely to enter inside the endoscope from the sealing portion such as O-rings and the steam is not accumulated in the inside. Therefore, improvement is achieved in order to increase durability.

Figure 8:
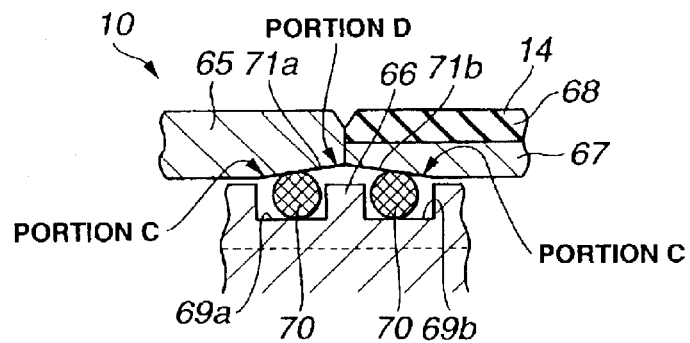
FIG. 8 to FIG. 11 relate to an endoscope according to a fourth embodiment of the present invention.

As shown in FIG. 8, a connector portion 10 of the endoscope 2 of the present embodiment is provided with a connector portion casing 65 which has the end portion in the shape of a cylinder and inside which a connector chassis member 66 is fitted.

A connector side folding-preventing member 14 is in contact with the end portion of the connector portion casing 65, and is fitted outside the connector chassis member 66.

Regarding the connector side folding-preventing member 14, a folding-preventing metal fitting 67 as an insert and a folding-preventing rubber 68 made of silicon rubber, etc., are integrally arranged by insert molding.

The connector chassis member 66 is provided with two O-ring grooves 69a and 69b, and these O-ring grooves 69a and 69b are provided with respective O-rings 70.

The sealing surface portions 71a and 71b which are in contact with the two O-ring grooves 69a and 69b and which are arranged on the connector portion casing 65 and folding-preventing metal fitting 67 are formed in the shape of a taper in order that the clearance of the inner side (portion C shown in the drawing) of the connector portion 10 becomes smaller than the clearance of the outer side (portion D shown in the drawing).

That is, the sealing surface portions 71a and 71b are formed in the shape of a taper in order that the inner diameters thereof become smaller with distances from both end portions of the connector portion casing 65 and the connector side folding-preventing member 14.

The clearance of the larger clearance side (portion D) is formed to have such a size that a gas does not leak at the maximum pressure during a leak test of the endoscope 2. In the present embodiment, the size is set such that a gas does not leak when the inside of the endoscope 2 is subjected to pressurization of 0.05 MPa.

The maximum pressure during a leak test performed generally in the market is 0.05 MPa. Other configuration is similar to that in the first embodiment.

Next, the actions of the present embodiment will be described.

Figure 9:
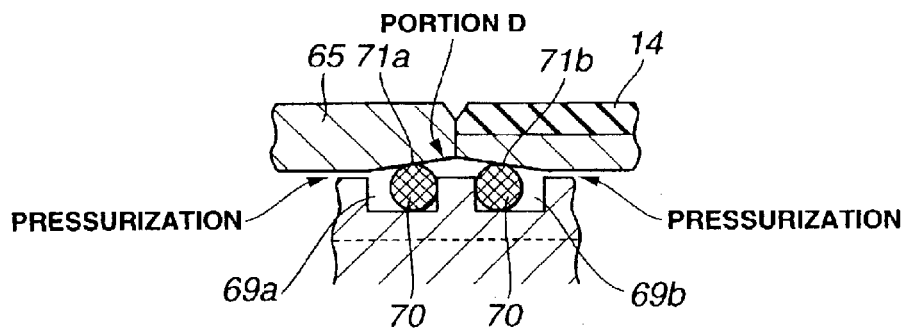
Figure 10:
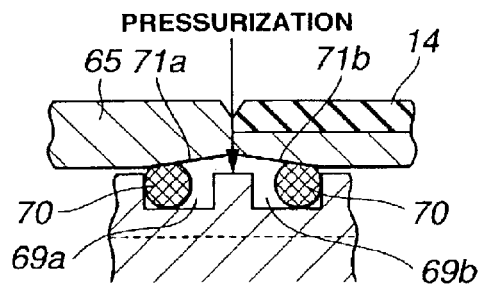

The actions specific to the present embodiment will be described with reference to FIG. 9 to FIG. 11.

It is assumed that a waterproof test of the endoscope 2 of the present embodiment is performed. As shown in FIG. 9, when the endoscope 2 is subjected to the waterproof test, pressurization is performed from a vent hole, not shown in the drawing, at 0.05 MPa.

According to this, the O-rings 70 move to the outer sides of the respective O-ring grooves 69a and 69b. Since each of the gaps of the outer side portions of the endoscope between the connector portion casing 65 and the O-ring groove 69a and between the connector side folding-preventing member 14 and the O-ring groove 69b is sealed by the O-rings 70, the gas does not leak and, therefore, a desired waterproof test can be performed.

Thereafter, the endoscope 2 is assumed to be subjected to a high-temperature high-pressure steam sterilization treatment. In this case, when pressurization is performed from the outside during the high-temperature high-pressure steam sterilization as shown in FIG. 10, since the O-rings 70 are pressed against the inner side having a small clearance of the endoscope and the squeeze ratio is increased, each of the gaps of the inner side portions of the endoscope between the connector portion casing 65 and the O-ring groove 69a and between the connector side folding-preventing member 14 and the O-ring groove 69b is sealed and, therefore, permeation of steam can be prevented.

Thereafter, it is assumed that a drying step including a step of depressurization of the high-temperature high-pressure steam sterilization is performed. In this drying step, when depressurization is performed from the outside as shown in FIG. 11, since the O-rings 70 are moved to the outer side having a large clearance of the endoscope 2 and the squeeze ratio is decreased, each of the gaps of the outer side portions of the endoscope between the connector portion casing 65 and the O-ring groove 69a and between the connector side folding-preventing member 14 and the O-ring groove 69b becomes in the non-sealed condition and, therefore, steam becomes likely to permeate. As a result, moisture inside the endoscope 2 is discharged and drying is performed.

The present embodiment has the following effect.

According to the present embodiment, effects similar to those in the aforementioned first embodiment can be achieved and, in addition to this, an endoscope in which steam is not accumulated inside the endoscope and which has excellent durability can be realized.

(Fifth Embodiment)

Initially, the configuration of the present embodiment will be described.

It is an object of the present embodiment to provide an inexpensive endoscope wherein the endoscope 2 is not broken even without a pressure control device. In order to realize the object, the endoscope in the aforementioned fourth embodiment is improved.

The overall configuration of the endoscope of the present embodiment is nearly similar to that in the aforementioned fourth embodiment, and different points are as shown below.

That is, the endoscope 2 of the present embodiment does not include such a pressure control device as the aforementioned waterproof cap 33 with a pressure control valve (refer to FIG. 1), and the endoscope 2 is sterilized in a hermetically sealed condition during high-temperature high-pressure steam sterilization.

That is, regarding the sealing surfaces 71a and 71b shown in FIG. 8, the clearance of the larger clearance side (portion D shown in FIG. 8) is formed to have such a size that a gas does not leak at the maximum pressure during a leak test of the endoscope, and is formed to have such a size that a gas leaks at a reduced pressure during the step of depressurization in the step of drying of high-temperature high-pressure steam sterilization.

The present embodiment is configured such that a gas does not leak when the pressure difference of 0.05 MPa is generated between the inside and the outside of the endoscope 2, the gas leaks when the pressure difference of 0.07 MPa is generated between the inside and the outside of the endoscope 2, and therefore, the gas begins to leak at, for example, 0.06 MPa. The aforementioned 0.07 MPa is a value based on the pressure decrease −0.07 MPa to 0.09 MPa during the step of depressurization in general high-temperature high-pressure steam sterilization apparatus.

Next, the actions of the present embodiment will be described.

Figure 11:
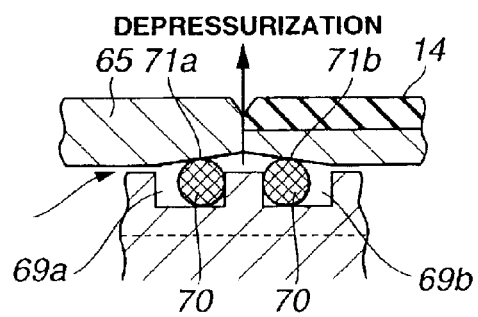

Regarding the endoscope of the present embodiment, the actions are nearly the same as those in the aforementioned fourth embodiment and, in addition, during performance of high-temperature high-pressure steam sterilization, when depressurization is performed in the prevacuum step, for example, depressurization of 0.07 MPa is performed, as shown in FIG. 11, the O-rings are pressed toward the outer side having a large clearance of the endoscope, the squeeze ratio is decreased, the internal pressure is released and, therefore, rupture of the soft coating, etc., covering the curve portion 16, and the like is prevented.

When depressurization is performed in the drying step, for example, depressurization of 0.07 MPa is performed, the internal pressure is released in a manner similar to that in the above description and, in addition, the steam permeated inside the endoscope 2 during high-temperature high-pressure steam sterilization is discharged.

The present embodiment has the following effect.

According to the present embodiment, nearly the same effects as those in the aforementioned fourth embodiment can be achieved and, in addition to this, an inexpensive endoscope wherein the endoscope 2 is not broken even without a pressure control device can be realized. Furthermore, an endoscope having excellent durability can be realized, wherein even when the pressure control device is prepared, but it is forgotten to mount this, the endoscope 2 is not broken.

(Sixth Embodiment)

The sixth embodiment of the present invention will be described with reference to FIG. 12 to FIG. 14. Initially, the configuration of the present embodiment will be described.

It is an object of the present embodiment to provide an endoscope which has excellent durability with respect to high-temperature high-pressure steam sterilization and in which the insertion portion does not acquire tendency to curve due to high-temperature high-pressure steam sterilization. In order to realize the object, improvement is achieved.

Figure 12:
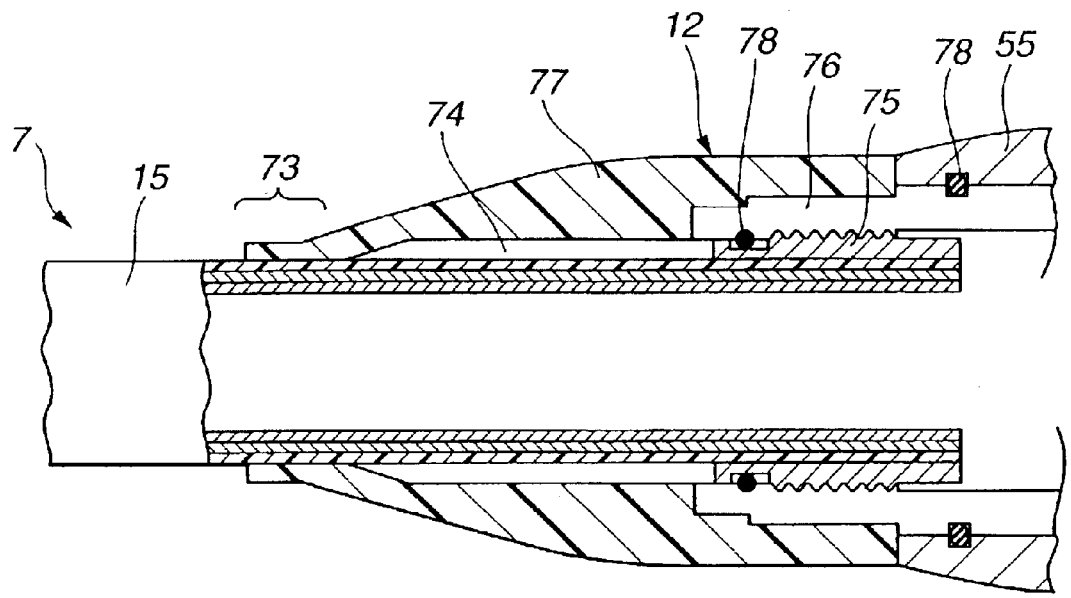
FIG. 12 to FIG. 14 relate to a sixth embodiment of the present invention.

In the endoscope of the present embodiment, as shown in FIG. 12, the insertion portion folding-preventing member 12 arranged on the insertion side of the operating portion 2 is configured by integrally molding a folding-preventing metal fitting 76 as an insert and a folding-preventing rubber 77 made of silicon rubber, etc., by insert molding.

A sealing portion 73 on the tip side of the folding-preventing rubber 77 is fitted liquid-tight to a flexible tube portion 15. This sealing portion 73 is configured to be liquid-tight against an external pressure from atmospheric pressure to on the order of +0.05 Mpa.

A connection base 75 is connected liquid-tight and fixed to the end portion of the flexible tube portion 15. This connection base 75 and the folding-preventing metal fitting 76 are mechanically fixed.

O-rings 78 are arranged between the folding-preventing metal fitting 76 and the operating portion casing 55 and between the folding-preventing metal fitting 76 and the connection base 75, respectively.

According to such a configuration, a liquid-tight space 74 is formed between the insertion portion folding-preventing member 12 on the side nearer to the operating portion 8 than is the sealing portion 73 and the outer perimeter of the flexible tube portion 15.

Figure 13:
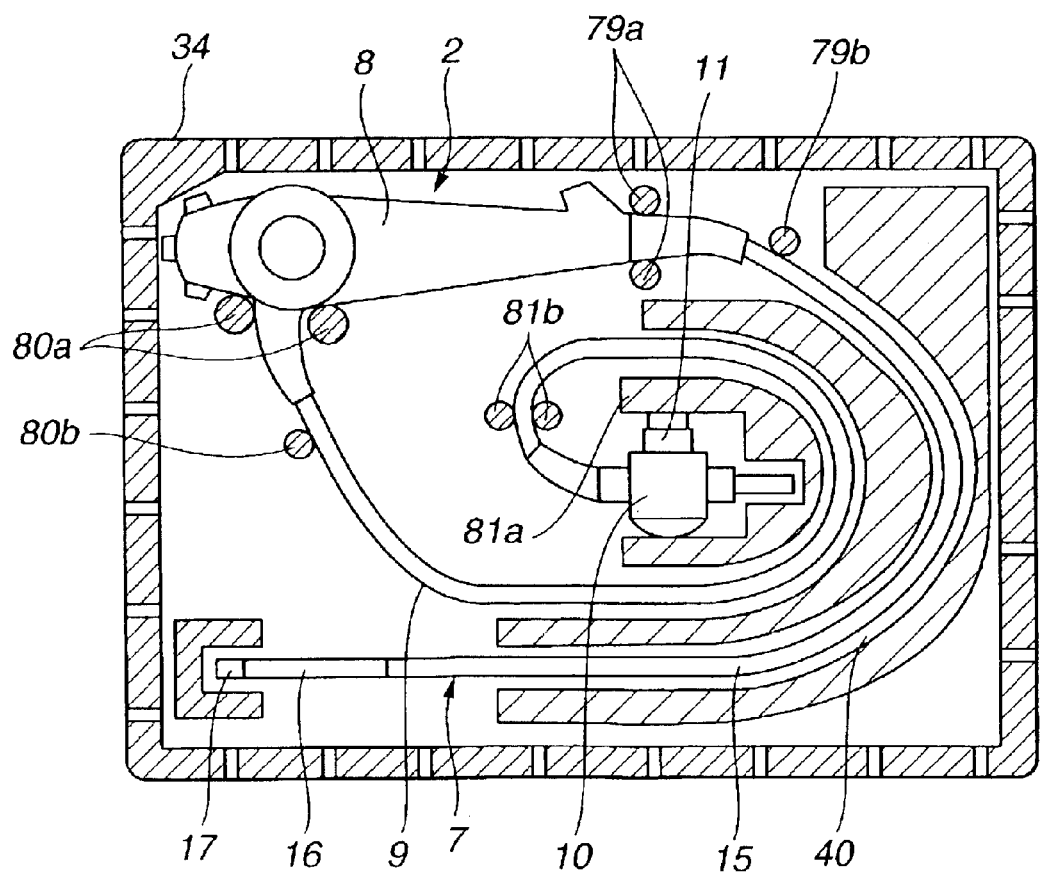

On the other hand, as shown in FIG. 13, the aforementioned endoscope is stored in a storage case for sterilization, and is subjected to a high-temperature high-pressure steam sterilization treatment.

As shown in FIG. 13, the sterilization storage case 34 used in the present embodiment is provided with regulation portions 79a and 79b as a regulation means.

Figure 14:
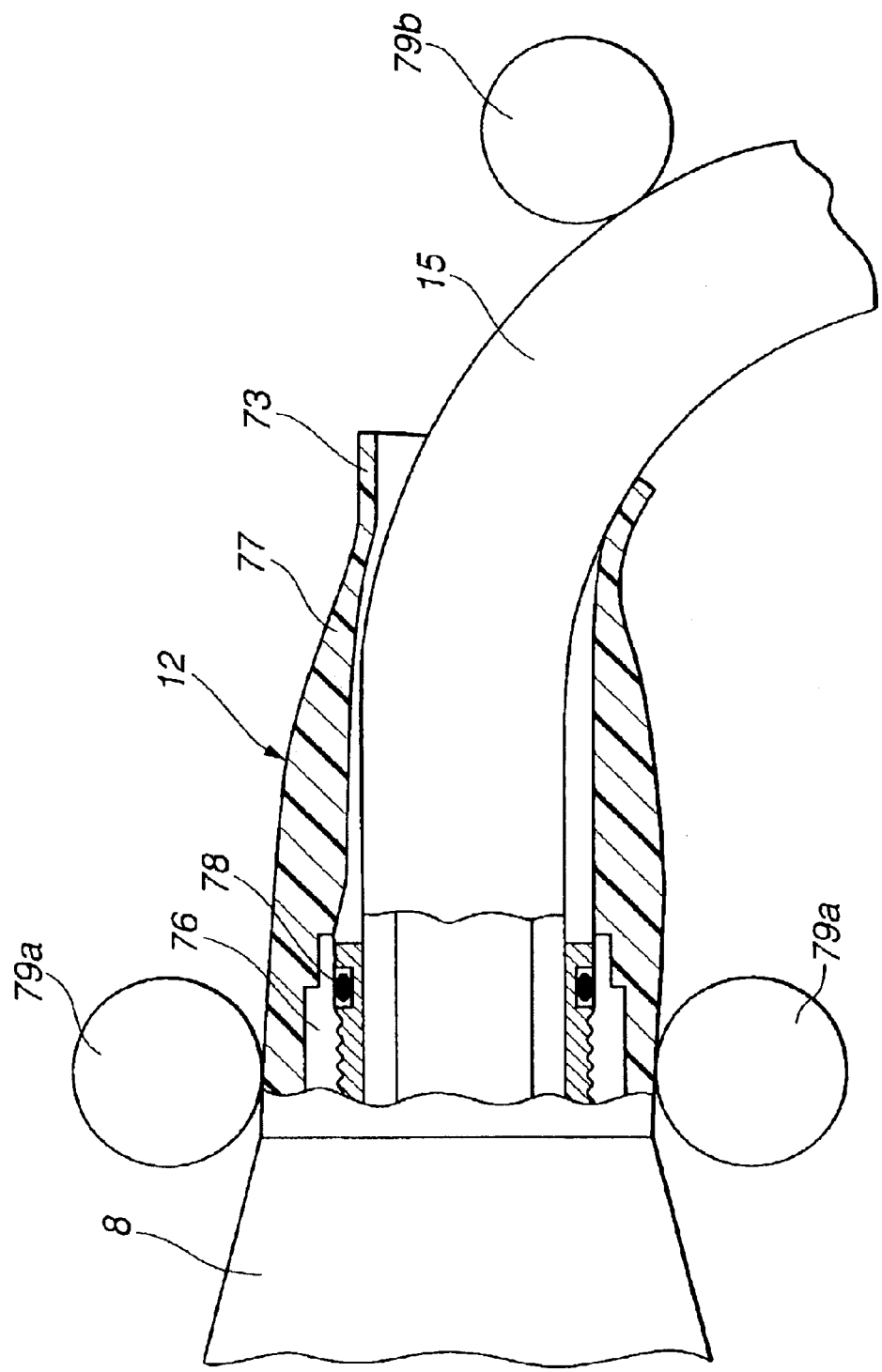

As shown in FIG. 13 and FIG. 14, the regulation portions 79a and 79b are formed such that when the endoscope 2 is stored in the sterilization storage case 34, a part of the operating portion 8 or the insertion portion folding-preventing member 12 on the operating portion 8 side is regulated and the location of the tip side of the flexible tube portion 15 or the insertion portion folding-preventing member 12 is regulated, and therefore, a gap is formed at a part of between the outer surface of the flexible tube portion 15 and the sealing portion 73 of the insertion portion folding-preventing member 12.

The sterilization storage case 34 is provided with an insertion portion regulation portion 40 where a certain range of the flexible tube portion 15 is forced to arrange linearly (refer to FIG. 13).

Furthermore, in the present embodiment, in order to position the operating portion folding-preventing member 13 and the connector side folding-preventing member 14, regulation portions 80a, 80b, 81a, and 81b are arranged at predetermined positions in the sterilization storage case 34 as the configuration similar to the aforementioned regulation portions 79a and 79b.

In the configuration of the present embodiment, the regulation portions as the regulation means may not be arranged in the sterilization storage case 34, but, for example, these regulation portions 79a and 79b may be arranged on a member different from the sterilization storage case, and this member may be stored in the sterilization storage case 34 so as to regulate positioning of the endoscope.

Next, the actions of the present embodiment will be described.

In the endoscope of the present embodiment, although steam enters into the space 74 (refer to FIG. 12) in the insertion portion folding-preventing member 12 due to high-temperature high-pressure steam sterilization, the steam in the aforementioned space 74 is discharged to the outside during the steps of depressurization in the prevacuum step and the drying step.

Regarding the high-temperature high-pressure steam sterilization method having no steps of depressurization, when the endoscope 2 is left standing after completion of sterilization for a certain time while being stored in the sterilization storage case 34, the steam in the space 74 of the insertion portion folding-preventing member 12 is dried.

According to this, moisture is not accumulated in the space 74 of the insertion portion folding-preventing member 12 and, therefore, corrosion of metallic members inside the space 74 and degradation of the outer sheath resin of the flexible tube portion 15 can be prevented. The insertion portion regulation portion 40 maintains the certain range of the flexible tube portion 15 forced to bend by the aforementioned regulation portions 79a and 79b in the linear condition and prevents this portion from acquiring tendency to curve.

Other actions are similar to those in the aforementioned first embodiment.

The present embodiment has the following effect.

According to the present embodiment, nearly the same effects as those in the aforementioned first embodiment can be achieved and, in addition to this, an endoscope which has excellent durability against high-temperature high-pressure steam sterilization and in which the insertion portion does not acquire tendency to curve due to high-temperature high-pressure steam sterilization can be realized.

The endoscope 2 of the present invention is not limited to the aforementioned first to sixth embodiments, and various modification can be performed within the scope of the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
   a slender insertion portion;
   an illuminational optical system which is arranged at the tip portion of the insertion portion and which emits transmitted illumination light onto a subject side;
   a first frame member provided with the illuminational optical system;
   an observational optical system for forming an optical image of the subject illuminated by the illuminational optical system;
   a second frame member provided with the observational optical system;
   a liquid-tight joint portion which is arranged at the end portion facing the outside of the first frame member and which is joined liquid-tight to a first lens member constituting the illuminational optical system and the first frame member; and
   a steam-tight joint portion which is arranged at the end portion facing the outside of the second frame member and which joins steam-tight a second lens member constituting the observational optical system and the second frame member, wherein the steam-tight joint portion has a characteristic different from that of the liquid-tight portion.

2. The endoscope according to claim 1, wherein the steam-tight joint portion is formed by sealing a metal layer arranged on the outer perimeter surface of the second lens member and the inner perimeter surface of the second frame member nearly fitted with the metal layer with a fused metal.

3. The endoscope according to claim 1, wherein the liquid-tight joint portion is formed by sealing the outer perimeter surface of the first lens member and the inner perimeter surface of the first frame member nearly fitted with the outer perimeter surface with an adhesive.

4. The endoscope according to claim 2, wherein the sealing with the fused metal is sealing with fused solder or sealing by fusing the metal layer or a metal film arranged on the inner perimeter surface of the second frame member nearly fitted with the metal layer by application of laser light to the second frame member nearly fitted with the metal layer.

5. The endoscope according to claim 1, wherein a solid image pickup element for photoelectric conversion is arranged at the image-forming position of the observational optical system.

6. The endoscope according to claim 1, wherein regarding the observational optical system, a solid image pickup element for photoelectric conversion is intimately joined to the surface on the light emission side of the observational optical system with an adherent optical element therebetween or without the adherent optical element therebetween.

7. The endoscope according to claim 1, wherein the steam-tight joint portion has a function of keeping steam-tightness with respect to the pressure difference of on the order of 0.2 Mpa or more.

8. The endoscope according to claim 1, wherein the liquid-tight joint portion has a function of keeping liquid-tightness with respect to the pressure difference of on the order of 0.05 Mpa or more.

9. The endoscope according to claim 1, wherein the second frame member comprises a first and second cylindrical members fitted to each other so as to become free to move, and includes a second steam-tight joint portion in which the fitted portion of the first and second cylindrical members is joined steam-tight with a fused metal.

10. The endoscope according to claim 9, wherein the second steam-tight joint portion is formed in the condition that the focus of the observational optical system is adjusted.

11. The endoscope according to claim 1, wherein the endoscope is formed to be adaptable to high-temperature high-pressure steam sterilization.

12. The endoscope according to claim 11, wherein even when steam enters into the liquid-tight joint portion due to the high-temperature high-pressure steam sterilization, the entered steam is discharged by the heat accompanying illumination light supplied to the illuminational optical system.

13. An endoscope comprising:

a slender insertion portion;

an illuminational optical system which is arranged at the tip portion of the insertion portion and which emits transmitted illumination light onto a subject side; and an observational optical system which is arranged at the tip portion of the insertion portion and which forms an optical image of the subject illuminated by the illumination light; wherein the steam-tight level of a first joint portion distinguishing the illuminational optical system from the outside of the endoscope or an internal space of the endoscope is specified to be lower than the steam-tight level of a second joint portion distinguishing the observational optical system from the outside of the endoscope or an internal space of the endoscope.

14. The endoscope according to claim 13, wherein the illuminational optical system is mounted to a first frame member, the observational optical system is mounted to a second frame member, and junctions are performed such that the steam-tight level of a first joint portion formed by a first lens member constituting the illuminational optical system being joined to the first frame member is lower than the steam-tight level of a second joint portion formed by a second lens member being joined to the second frame member constituting the observational optical system.

15. The endoscope according to claim 14, wherein a layer made of gold or an gold alloy is formed on the joint surface of the second lens member and the second frame member made of a metal, and the layer is fused by application of laser light so as to perform steam-tight junction, while the joint portion of the first lens member of the illuminational optical system and the first frame member is joined with an adhesive so as to form the steam-tight level of the first joint portion.

16. The endoscope according to claim 14, wherein a metallized layer capable of being soldered is formed on the joint surface of the first lens member, and the metallized layer and the second frame member made of a metal are soldered so as to join steam-tight, while the joint portion of the first lens member and the first frame member is joined with an adhesive so as to form the first joint portion.

17. The endoscope according to claim 13, wherein a water supply nozzle is formed at the tip portion, and is arranged such that a tip lens member of the illuminational optical system is not included in the range of water supplied from the water supply nozzle.

18. The endoscope according to claim 13, wherein the endoscope is formed to be adaptable to high-temperature high-pressure steam sterilization.

19. The endoscope according to claim 13, wherein the pressure resistance of the first joint portion to prevent entering of steam into the observational optical system is formed to be on the order of 0.2 Mpa or more.

20. The endoscope according to claim 19, wherein the pressure resistance of the second joint portion to prevent entering of liquid into the illuminational optical system is specified to be on the order of 0.05 Mpa or more.

21. The endoscope according to claim 1, wherein the liquid-tight joint portion is not steam-tight starting at pressures exceeding 0.2 MPa.

* * * * *